United States Patent [19]

Schneider

[11] Patent Number: 4,965,390

[45] Date of Patent: Oct. 23, 1990

[54] HYDROXAMIC ACID ESTERS

[75] Inventor: Hans-Dieter Schneider, Weil am Rhein, Fed. Rep. of Germany

[73] Assignee: Ciba-Geigy Corporation, Ardsley, N.Y.

[21] Appl. No.: 474,422

[22] Filed: Feb. 2, 1990

[51] Int. Cl.$^5$ .............................................. C07C 83/10
[52] U.S. Cl. ............................................................ 558/7
[58] Field of Search .................................................. 558/7

[56] References Cited

U.S. PATENT DOCUMENTS

| | | | |
|---|---|---|---|
| 4,150,043 | 4/1979 | Gebert | 558/7 |
| 4,404,384 | 9/1983 | Gebert | 558/7 |
| 4,743,701 | 5/1988 | Mathew | 558/7 |
| 4,909,835 | 3/1990 | Tobler | 558/7 |

FOREIGN PATENT DOCUMENTS

| | | |
|---|---|---|
| 0243313 | 4/1987 | European Pat. Off. . |
| 2651083 | 5/1978 | Fed. Rep. of Germany . |
| 3220106 | 5/1982 | Fed. Rep. of Germany .......... 558/7 |

*Primary Examiner*—John M. Ford
*Assistant Examiner*—Robert C. Whittenbaugh
*Attorney, Agent, or Firm*—Kevin T. Mansfield; Edward McC.Roberts

[57] ABSTRACT

O-substituted hydroxylamines of the formula I

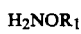 (I)

$H_2NOR_1$ in which
$R_1$ is $C_1$–$C_6$alkyl, $C_1$–$C_6$ haloakyl, $-CH_2CR_2=CR_3R_4$ or $-CH_2C\equiv CR_5$;
$R_2$ is hydrogen, halogen or methyl;
$R_3$ is hydrogen, halogen or methyl;
$R_4$ is hydrogen, halogen or methyl; and
$R_5$ is hydrogen, methyl or ethyl,
are prepared by reacting a nitrile of the formula II $R_6-CN$    (II)

in which $R_6$ is $C_1$–$C_4$alkyl, phenyl or benzyl, is reacted with an alcohol of the formula III $R_7-OH$    (III)

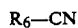

in which $R_7$ is $C_1$–$C_5$alkyl, benzyl or $C_1$–$C_4$alkoxyethyl, in an organic solvent which is only sparingly miscible with water or not at all, in the presence of hydrogen halide HX, the suspension obtained of the iminoester hydrohalide of the formula IV

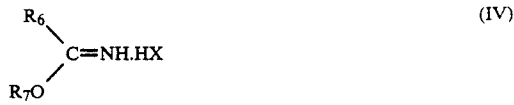 (IV)

in which $R_6$ and $R_7$ are as defined above and X is chlorine, bromine or iodine, is added at a controlled rate to an aqueous suspension of a carbonate or hydrogen carbonate at a temperature of from $-3°$ to $+5°$ C., an aqueous solution of a hydroxylamine salt is added to the mixture obtained at a temperature of from $-20°$ to $-5°$ C., the aqueous phase is separated off after the mixture has been warmed to room temperature, the solution obtained of the hydroximic acid ester of the formula V

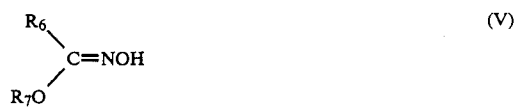 (V)

in which $R_6$ and $R_7$ are as defined above, in an organic solvent is first treated with an aqueous solution of a strong base and then with an alkylating agent of the formula VI

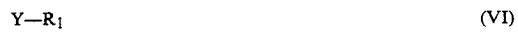

$Y-R_1$    (VI)

in which $R_1$ is as defined above and Y is chlorine, bromine, iodine or $-O-SO_2R_8$, and $R_8$ is $C_1$–$C_4$alkyl, $C_1$–$C_4$ haloalkyl, phenyl or phenyl-substituted $C_1$–$C_4$alkyl, it being possible for the phenyl ring itself to be monosubstituted, disubstituted or trisubstituted by halogen or $C_1$–$C_4$alkyl, and Y is alternatively—$OSO_2OR_1$ if $R_1$ is $C_1$–$C_2$alkyl, at from room temperature to the boiling point of the reaction mixture, the mixture is cooled to room temperature when the O-alkylation is complete, the aqueous phase is separated off, the oxime ether of the formula VII

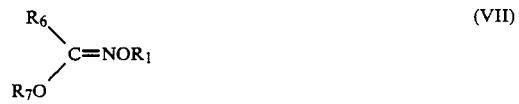 (VII)

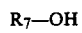

in which $R_1$, $R_6$ and $R_7$ are as defined above, formed is hydrolysed by stirring with an aqueous solution of a strong acid, and the aqueous phase containing the salt of the O-substituted hydroxylamine of the formula I is separated off, and the hydroxylamine of the formula I is isolated, if necessary, by evaporating the water.

6 Claims, No Drawings

HYDROXAMIC ACID ESTERS

The present invention relates to a process for the preparation of O-substituted hydroxylamines of the formula I $$H_2NOR_1 \quad (I)$$

in which
$R_1$ is $C_1$-$C_6$alkyl, $C_1$-$C_6$haloalkyl, $-CH_2CR_2=CR_3R_4$ or $-CH_2C\equiv CR_5$;
$R_2$ is hydrogen, halogen or methyl;
$R_3$ is hydrogen, halogen or methyl;
$R_4$ is hydrogen, halogen or methyl; and
$R_5$ is hydrogen, methyl or ethyl,
and intermediates produced at some stage in this process.

The O-substituted hydroxylamines of the formula I are valuable intermediates in the preparation of herbicidally active acylcyclohexanediones, as disclosed, for example, in European Patent Application No. 0,243,313.

Preparation processes for O-substituted hydroxylamines and their precursors are described in the literature.

U.S. Pat. No. 4,743,701 discloses to prepare hydroximic acid esters of the formula $$\begin{array}{c} R_9 \\ \phantom{R_{10}O}\diagdown \\ \phantom{xxxx}C=NOH \\ \phantom{R_{10}O}\diagup \\ R_{10}O \end{array} \quad (VIII)$$

in which $R_9$ and $R_{10}$, independently of one another, are alkyl, cycloalkyl, aryl or aralkyl, by reacting, in a first step, a nitrile of the formula $R_9CN$ under anhydrous conditions with an alcohol of the formula $R_{10}$-OH in an organic solvent in the presence of hydrogen halide to give the corresponding imidate hydrohalide, separating off the solid imidate hydrohalide from the reaction mixture and subsequently reacting this, in a second step, under anhydrous conditions in an organic solvent with a hydroxylamine salt and with ammonia gas to give the hydroximic acid ester of the formula VIII.

German Offenlegungsschrift No. 2,651,083 discloses to prepare O-substituted hydroxylamines of the formula IX $$H_2N-O-CH_2-\underset{\underset{OH}{|}}{CH}-CH_2R_{12} \quad (IX)$$

in which $R_{12}$ is an ether, thiol, phenol or thiophenol radical or an amino group, by reacting a hydroximic acid ester of the formula X $$\begin{array}{c} R_{11} \\ \phantom{R_{13}O}\diagdown \\ \phantom{xxxx}C=NOH \\ \phantom{R_{13}O}\diagup \\ R_{13}O \end{array} \quad (X)$$

in which $R_{11}$ is an alkyl or aryl radical, with a 2-propanol of the formula XI $$Z-CH_2-\underset{\underset{OH}{|}}{CH}-CH_2R_{12} \quad (XI)$$

in which Z is halogen or a sulfonate group, in a non-aqueous medium in the presence of a base to give the O-substituted hydroximic acid esters of the formula XII $$\begin{array}{c} R_{11} \\ \phantom{R_{13}O}\diagdown \\ \phantom{xxxx}C=N-O-CH_2-\underset{\underset{OH}{|}}{CH}-CH_2R_{12} \\ \phantom{R_{13}O}\diagup \\ R_{13}O \end{array} \quad (XII)$$

and subsequently removing the protecting group hydrolytically.

However, these known processes have a number of disadvantages. Thus, for example, gaseous ammonia must be used for the preparation of the hydroximic acid esters of the formula VIII in accordance with U.S. Pat. No. 4,743,701, due to which large amounts of undesired ammonium salts are produced as a byproduct. Besides the economically disadvantageous way in which the reaction is carried out in several steps, the anhydrous procedure in the 2nd process step means that large amounts of organic solvents are produced, whose recycling or disposal means additional costs.

The O-substituted hydroximic acid esters of the formula XII disclosed in German Offenlegungsschrift No. 2,651,083 likewise require an ecologically unfavourable anhydrous procedure for their preparation. The hydroximic acid esters of the formula X required as starting materials for this process must previously be prepared in a separate process.

It has now been found that the O-substituted hydroxylamines of the formula I can be prepared in good yield and purity in an economically and ecologically particularly advantageous manner when a nitrile of the formula II $$R_6-CN \quad (II)$$

in which $R_6$ is $C_1$-$C_4$alkyl, phenyl or benzyl, is reacted with an alcohol of the formula III $$R_7-OH \quad (III)$$

in which $R_7$ is $C_1$-$C_5$alkyl, benzyl or $C_1$-$C_4$alkoxyethyl, in an organic solvent which is only sparingly miscible with water or not at all, in the presence of hydrogen halide HX, the suspension obtained of the iminoester hydrohalide of the formula IV $$\begin{array}{c} R_6 \\ \phantom{R_7O}\diagdown \\ \phantom{xxxx}C=NH.HX \\ \phantom{R_7O}\diagup \\ R_7O \end{array} \quad (IV)$$

in which $R_6$ and $R_7$ are as defined above and X is chlorine, bromine or iodine, is added at a controlled rate to an aqueous suspension of a carbonate or hydrogen carbonate at a temperature of from $-3°$ to $+5°$ C., an aqueous solution of a hydroxylamine salt is added to the mixture obtained at a temperature of from $-20°$ to $-5°$ C., the aqueous phase is separated off after the mixture has been warmed to room temperature, the solution obtained of the hydroximic acid ester of the formula V

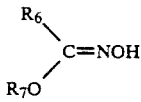  (V)

in which $R_6$ and $R_7$ are as defined above, in an organic solvent is first treated with an aqueous solution of a strong base and then with an alkylating agent of the formula VI $$Y—R_1 \quad (VI)$$

in which $R_1$ is as defined above and Y is chlorine, bromine, iodine or $—O—SO_2R_8$, and $R_8$ is $C_1$-$C_4$alkyl, $C_1$-$C_4$haloalkyl, phenyl or phenyl-substituted $C_1$-$C_4$alkyl, it being possible for the phenyl ring itself to be monosubstituted, trisubstituted by halogen or $C_1$-$C_4$alkyl, and Y is alternatively $—OSO_2OR_1$ if $R_1$ is $C_1$-$C_2$alkyl, at from room temperature to the boiling point of the reaction mixture, the mixture is cooled to room temperature when the O-alkylation is complete, the aqueous phase is separated off, the oxime ether of the formula VII

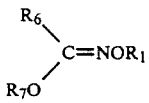  (VII)

in which $R_1$, $R_6$ and $R_7$ are as defined above, formed is hydrolysed by stirring with an aqueous solution of a strong acid, and the aqueous phase containing the salt of the O-substituted hydroxylamine of the formula I is separated off, and the hydroxylamine of the formula I is isolated, if necessary, by evaporating the water.

The alkyl groups occurring in the substituents may be straight-chain or branched and are, for example, methyl, ethyl, n-propyl, iso-propyl, n-butyl, iso-butyl, sec-butyl, tert-butyl, n-pentyl or the isomeric pentyl radicals, n-hexyl or the isomeric hexyl radicals. Alkyl radicals having a maximum of 4 carbon atoms, in particular methyl and ethyl, are preferred.

The phenyl and benzyl groups occurring in the substituent $R_6$ may be unsubstituted or substituted by halogen, nitro, $C_1$-$C_4$alkyl or $C_1$-$C_4$haloalkyl, for example 2-chlorophenyl, 3-chlorophenyl, 4-chlorophenyl, 2,4-dichlorophenyl, 4-fluorophenyl, 4-methylphenyl, 2,4-dimethylphenyl, 4-methylbenzyl, 4-nitrobenzyl, 4-trifluoromethylphenyl or 4-bromobenzyl.

Alkoxy is to be understood as meaning: methoxy, ethoxy, n-propxy, iso-propoxy or the four isomeric butoxy radicals, but in particular methoxy or ethoxy.

Halogen, itself or as part of a substituent such as haloalkyl, is fluorine, chlorine, bromine and iodine, preferably chlorine and bromine. Haloalkyl is generally chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 2-chloroethyl and 3-chloropropyl, but in particular fluoromethyl, chloromethyl, difluoromethyl and trifluoromethyl.

Examples of phenyl-substituted $C_1$-$C_4$alkyl groups are 4-phenylbutyl, 2-phenylethyl or benzyl. Examples of phenyl groups which are substituted by halogen or $C_1$-$C_4$alkyl are 4-bromophenyl, 2,4-dichlorophenyl, 2,4,6-trichlorophenyl, 4-fluorophenyl, 4-methylphenyl, 2,4-dimethylphenyl, 4-ethylphenyl or 4-iso-propylphenyl. Preferred phenyl groups substituted by the above-mentioned radicals are 4-bromophenyl and 4-methylphenyl.

Organic solvents which are only sparingly (up to 10% by weight) miscible with water or not at all and which are suitable for the process according to the invention are toluene, hexane, diethyl ether, xylene, cyclohexane, nitrobenzene, dichloroethane, dichloromethane or trichloromethane. A very particularly preferred solvent is toluene.

Carbonates or hydrogen carbonates employed in the process according to the invention for reaction with the iminoester hydrohalide of the formula IV are taken to mean, in particular, the alkali metal compounds, such as sodium carbonate, potassium carbonate, sodium hydrogen carbonate or potassium hydrogen carbonate. Sodium hydrogen carbonate is the most preferred.

The starting materials of the formulae II and III and the intermediates of the formulae IV, V and VI of the process according to the invention are known and in some cases commercially available.

The intermediates of the formula VII produced during the process according to the invention are novel, with the exception of those compounds in which $R_1$ is $C_1$-$C_6$alkyl, $C_1$-$C_6$haloalkyl or allyl, and likewise form a subject-matter of the present invention. If desired, the compounds of the formula VII can be isolated from the reaction medium for characterization purposes. If desired, the end products of the formula I can be obtained in free form by known methods by treatment with a base.

The reaction of the nitrile of the formula II with the alcohol of the formula III to give the iminoester hydrohalide of the formula IV is generally carried out at temperatures of from $-10°$ to $+30°$ C., preferably $0°$ to $25°$ C. The preferred hydrogen halide HX here is hydrogen chloride. Before further reaction, the imidate hydrohalide reaction mixture can if desired be freed from unreacted hydrogen chloride by evacuation or by passing in nitrogen.

Examples of hydroxylamine salts which are suitable for the process according to the invention are hydroxylamine hydrochloride, hydroxylamine sulfate and hydroxylamine phosphate, with hydroxylamine hydrochloride and hydroxylamine sulfate being the most preferred.

The alkylation of the hydroximic acid ester of the formula V is carried out at temperatures of from room temperature to the boiling point of the reaction mixture. A preferred temperature range is between $+50°$ and $80°$ C. Suitable strong bases for this process step are aqueous carbonates and hydroxides of alkali metals and alkaline earth metals. Preferred strong bases are aqueous sodium hydroxide and aqueous sodium carbonate. The hydroximic acid ester of the formula V, the alkylating agent of the formula VI and the base are preferably employed in equimolar amounts.

The alkylation is advantageously carried out in the presence of catalytic amounts of a phase-transfer catalyst. The phase-transfer catalyst is advantageously employed in an amount of from 0.01 to 10 mol %, preferably 0.5 to 1 mol %, based on the compound of the formula V.

Suitable phase-transfer catalysts are, in general, quaternary ammonium salts and crown ethers. Preferred phase-transfer catalysts are 18-crown-6, benzyltrimethylammonium chloride, tetrabutylammonium chloride, tetramethylammonium sulfate, tetramethylammonium chloride and tetrabutylammonium bromide. Tetrabutylammonium bromide is the most preferred.

The alkylation can be carried out particularly advantageously by using, as alkylating agent, a compound of the formula VI in which Y is chlorine, bromine, iodine, 4-methylphenylsulfonyl, 4-bromophenylsulfonyl or methylsulfonyl, but in particular chlorine, bromine or iodine.

Particularly advantageous compounds of the formula I in which $R_1$ is $-CH_2CR_2=CR_3R_4$, where $R_2$, $R_3$ and $R_4$, independently of one another, are preferably hydrogen, chlorine, bromine or methyl, are prepared by the process according to the invention.

Examples of strong acids which are suitable for the hydrolsis are mineral acids, such as hydrochloric acid, sulfuric acid or phosphoric acid; or sulfonic acids, such as methanesulfonic acid, benzenesulfonic acid or p-toluenesulfonic acid. Hydrochloric acid is the most preferred.

In the most preferred variant of the process according to the invention, acetonitrile and ethanol are reacted in toluene in the presence of hydrogen chloride, the suspension obtained is added at a controlled rate to an ice-cooled, aqueous suspension of sodium hydrogen carbonate, an aqueous solution of hydroxylamine sulfate is added to the mixture obtained at a temperature of from $-20°$ to $-5°$ C., the aqueous phase is separated off after the mixture has been warmed to room temperature, the solution obtained of ethyl acetohydroximate in toluene is treated first with an aqueous solution of sodium hydroxide and then with trans-1,3-dichloropropene at a temperature of from $+50°$ to $+80°$ C., the mixture is cooled to room temperature when the O-alkylation is complete, the aqueous phase is separated off, the ethyl O-(trans-chloroally)acetohydroximate formed is hydrolysed by stirring with dilute hydrochloric acid, and the aqueous phase containing the hydrochloride of O-(trans-chloroallyl)hydroxylamine is separated off and the latter is isolated, if necessary, by evaporating the water.

Using the process according to the invention, the compounds of the formula I can be prepared at low cost from readily accessible starting materials in good yields and high purity. Compared with the process disclosed in U.S. Pat. No. 4,743,701, only half the amount of undesired ammonium salts are produced as a byproduct by using sodium hydrogen carbonate as base.

It should furthermore be particularly advantageously emphasized that the process according to the invention is carried out without a solvent change and without isolating intermediates. This considerably reduces the amount of time and apparatus complexity compared with known processes.

The examples below serve to explain the process according to the invention in greater detail.

EXAMPLE 1

Preparation of ethyl acetohydroximate

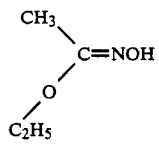

102 g of hydrogen chloride is passed over the course of two hours into a mixture of 116.6 g of acetonitrile and 125.6 g of absolute ethanol in 270 g of toluene at a temperature of from $+12°$ to $+15°$ C. The reaction mixture is subsequently stirred for 22 hours at a temperature of from $+20°$ to $+25°$ C. After the mixture has been cooled to $-10°$ C., 234.4 g of sodium hydrogen carbonate are added. A solution of 207.6 g of hydroxylamine sulfate in 630 ml of water is subsequently added dropwise over the course of one hour at a temperature of from $-10°$ to $-5°$ C., $CO_2$ evolution occurring. The reaction mixture is subsequently stirred for 90 minutes, warming slowly to room temperature. After the aqueous phase has been separated off, the organic phase is extracted with 200 ml of water. Separating off the aqueous phase gives a solution of 240.2 g of ethyl acetohydroximate (93.9% of theory) in toluene.

EXAMPLE 2

Preparation of O-(trans-chloroallyl)hydroxylamine hydrochloride (compound No. 1.1)

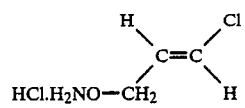 (1.1)

A solution, obtained as in Example 1, of 277.6 g of ethyl acetohydroximate in toluene (content: 39%) is added dropwise over the course of 25 minutes to a solution of 173 g of 30% sodium hydroxide solution in 173 ml of water. 3.2 g of tetrabutylammonium bromide are subsequently added to the suspension produced. 115.7 g of trans-1,3-dichloropropene (content: 96%) are added dropwise to this reaction mixture over the course of 30 minutes at a temperature of from $+60°$ to $+65°$ C. After the mixture has been warmed to a temperature between $+70°$ and $+75°$ C. for a period of 3 hours, the reaction mixture is cooled to room temperature and the aqueous phase is subsequently separated The organic phase, which contains the ethyl O-(trans-chloroallyl)acetohydroximate (compound No. 2.1), is extracted twice with 250 ml of water. The organic phase is subsequently added dropwise over the course of 2½ hours at a temperature of from $+20°$ to $+30°$ C. to a solution of 102.4 g of 32% hydrochloric acid in 54 ml of water. The reaction mixture is subsequently warmed at a temperature of from $+40°$ to 45° C. for a period of 2½ hours and cooled to room temperature, and the aqueous phase is separated off. 270.3 g (87.5% of theory, based on trans-1,3-dichloropropene) of O-(trans-chloroallyl)hydroxylamine (compound No. 1.1) in the form of its hydrochloride (content: 46.6%) are obtained in aqueous solution.

228 g of the aqueous phase are evaporated at a pressure of 400 to 500 Pa and a temperature of $+60°$ C. After the residue has been dried in vacuo at $+50°$ C., 108 g of O-(trans-choroallyl)hydroxylamine (compound No. 1.1) in the form of its hydrochloride with a content of 98.5% and a melting point of from +164° to +165° C. are obtained. After recrystallization from ethanol/diethyl ether, the melting point is +182° to +183° C.

The compounds listed in Tables 1 and 2 are prepared in corresponding manner to the procedures described above:

TABLE 1

$$H_2NOR_1 \cdot HCl \quad (I)$$

| Compound No. | $R_1$ | M.p. [°C.] |
|---|---|---|
| 1.1 | H, Cl / C=C / -CH$_2$, H | +182 to +183 |
| 1.2 | H, H / C=C / -CH$_2$, Cl | +175 to +176 |
| 1.3 | -CH$_2$-C(CH$_3$)=CH$_2$ | +165 |
| 1.4 | -CH$_2$-C(Cl)=CH$_2$ | |
| 1.5 | -CH$_2$-C(Br)=CH$_2$ | |
| 1.6 | H, CH$_3$ / C=C / -CH$_2$, H | +158 to +160 |
| 1.7 | -CH$_2$-CBr=CBrH | (cis/trans mixture) |
| 1.8 | -CH$_2$-CH=CCH$_3$Cl | (cis/trans mixture) |
| 1.9 | -CH$_2$-C≡CH | +152 to +153 |
| 1.10 | -CH$_3$ | +147 to +148 |
| 1.11 | -CH$_2$CH$_2$Cl | +180 to +181 |

TABLE 2

$$\begin{matrix} R_6 \\ R_7O \end{matrix} C = NOR_1 \quad (VII)$$

| Compound No. | $R_7$ | $R_6$ | $R_1$ | B.p. [°C.]/ Pressure [Pa] |
|---|---|---|---|---|
| 2.1 | C$_2$H$_5$ | CH$_3$ | H, Cl / C=C / -CH$_2$, H | 49–50°/200 |
| 2.2 | C$_2$H$_5$ | CH$_3$ | H, H / C=C / -CH$_2$, Cl | 68–69°/800 |
| 2.3 | C$_2$H$_5$ | CH$_3$ | -CH$_2$-C(CH$_3$)=CH$_2$ | 78°/5000 |
| 2.4 | C$_2$H$_5$ | CH$_3$ | -CH$_2$-C(Cl)=CH$_2$ | 79°/2200 |
| 2.5 | C$_2$H$_5$ | CH$_3$ | -CH$_2$-C(Br)=CH$_2$ | 77°/1100 |
| 2.6 | C$_2$H$_5$ | CH$_3$ | H, CH$_3$ / C=C / -CH$_2$, H | 60–61°/1000 |
| 2.7 | C$_2$H$_5$ | CH$_3$ | -CH$_2$CBr=CBrH | 89–90°/40 (cis/trans mixture) |
| 2.8 | C$_2$H$_5$ | CH$_3$ | -CH$_2$-CH=CCH$_3$Cl | 93°/1500 (cis/trans mixture) |
| 2.9 | C$_2$H$_5$ | CH$_3$ | -CH$_2$-C≡CH | 40°/500 |
| 2.10 | C$_2$H$_5$ | C$_2$H$_5$ | H, Cl / C=C / -CH$_2$, H | |

TABLE 2-continued $$\begin{array}{c} R_6 \\ \phantom{R_7O}\diagdown \\ \phantom{R_7O}C=NOR_1 \\ \diagup \\ R_7O \end{array} \quad (VII)$$

| Compound No. | $R_7$ | $R_6$ | $R_1$ | B.p. [°C.]/ Pressure [Pa] |
|---|---|---|---|---|
| 2.11 | $C_2H_5$ | $i\text{-}C_3H_8$ | 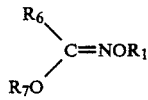 | |
| 2.12 | $C_2H_5$ | Phenyl | $-CH_2-\underset{\underset{CH_3}{\vert}}{C}=CH_2$ | |
| 2.13 | $C_2H_5$ | Benzyl | $-CH_2-\underset{\underset{Cl}{\vert}}{C}=CH_2$ | |
| 2.14 | $CH_3$ | $CH_3$ | $-CH_2-\underset{\underset{Br}{\vert}}{C}=CH_2$ | |
| 2.15 | $i\text{-}C_3H_8$ | $CH_3$ | $\begin{array}{c} H \phantom{xx} CH_3 \\ \diagdown \phantom{x} \diagup \\ C=C \\ \diagup \phantom{x} \diagdown \\ -CH_2 \phantom{xx} H \end{array}$ | |
| 2.16 | Benzyl | $CH_3$ | $-CH_2CBr=CBrH$ | |
| 2.17 | $C_2H_5$ | $CH_3$ | $-CH_3$ | +106 to +107 |
| 2.18 | $C_2H_5$ | $CH_3$ | $-CH_2CH_2Cl$ | +41/250 |
| 2.19 | $CH_3OCH_2CH_2-$ | $CH_3$ | $-CH_2-C\equiv CH$ | |

What is claimed is:

1. A compound of the formula VII $$\begin{array}{c} R_6 \\ \phantom{R_7O}\diagdown \\ \phantom{R_7O}C=NOR_1 \\ \diagup \\ R_7O \end{array} \quad (VII)$$

in which
$R_7$ is $C_1$-$C_5$alkyl, benzyl or $C_1$-$C_4$alkoxyethyl;
$R_6$ is $C_1$-$C_4$alkyl, phenyl or benzyl;
$R_1$ is $-CH_2CR_2=CR_3R_4$ or $-CH_2C\equiv CR_5$;
$R_2$ is hydrogen, halogen or methyl;
$R_3$ is hydrogen, halogen or methyl;
$R_4$ is hydrogen, halogen or methyl and
$R_5$ is hydrogen, methyl or ethyl, with the proviso that $R_2$, $R_3$ and $R_4$ are not simultaneously hydrogen.

2. A compound of the formula VII according to claim 1, wherein $R_7$ and $R_6$, independently of one another, are $C_1$-$C_2$alkyl.

3. A compound of the formula VII according to claim 1, wherein $R_1$ is $-CH_2CR_2=CR_3R_4$.

4. A compound of the formula VII according to claim 1, wherein $R_2$, $R_3$ and $R_4$, independently of one another, are hydrogen, chlorine, bromine or methyl.

5. A compound of the formula VII according to claim 1, wherein $R_1$ is chloroallyl.

6. Ethyl O-(trans-chloroallyl)acetohydroximate according to claim 1.

* * * * *